(12) United States Patent
Burnett et al.

(10) Patent No.: US 8,439,960 B2
(45) Date of Patent: May 14, 2013

(54) HYPOTHERMIA DEVICES AND METHODS

(75) Inventors: Daniel Rogers Burnett, San Francisco, CA (US); Gregory W. Hall, Redwood City, CA (US)

(73) Assignee: Velomedix, Inc., Menlo Park, CA (US)

( * ) Notice: Subject to any disclaimer, the term of this patent is extended or adjusted under 35 U.S.C. 154(b) by 1276 days.

(21) Appl. No.: 12/169,566

(22) Filed: Jul. 8, 2008

(65) Prior Publication Data

US 2009/0076573 A1  Mar. 19, 2009

Related U.S. Application Data

(60) Provisional application No. 60/958,717, filed on Jul. 9, 2007.

(51) Int. Cl.
*A61F 7/12* (2006.01)

(52) U.S. Cl.
USPC ............... 607/105; 604/6.13; 607/104

(58) Field of Classification Search ........... 604/6.13, 604/6.16, 27, 29, 113, 508; 607/104, 105
See application file for complete search history.

(56) References Cited

U.S. PATENT DOCUMENTS

| | | |
|---|---|---|
| 2,078,786 A | 4/1937 | Wood |
| 3,042,042 A | 7/1962 | Blanck |
| 3,505,988 A | 4/1970 | Deane |
| 3,698,396 A | 10/1972 | Katerndahl et al. |
| 3,927,980 A | 12/1975 | Leonard |
| 4,302,972 A | 12/1981 | Oettle et al. |
| 4,356,826 A | 11/1982 | Kubota |
| 4,413,633 A | 11/1983 | Yanda |
| 4,424,806 A * | 1/1984 | Newman et al. ............... 601/41 |
| 4,445,500 A | 5/1984 | Osterholm |
| 4,450,841 A | 5/1984 | Osterholm |
| 4,497,324 A | 2/1985 | Sullivan et al. |
| 4,535,773 A | 8/1985 | Yoon |
| 4,808,157 A | 2/1989 | Coombs |
| 4,813,429 A | 3/1989 | Eshel et al. |
| 4,883,459 A | 11/1989 | Calderon |
| 4,904,237 A | 2/1990 | Janese |
| 4,919,134 A | 4/1990 | Streeter |

(Continued)

FOREIGN PATENT DOCUMENTS

| | | |
|---|---|---|
| EP | 2135552 A1 | 12/2009 |
| GB | 2267829 A | 12/1993 |

(Continued)

OTHER PUBLICATIONS

Sedlak, S. Kay; Hypothermia in trauma: the nurse's role in recognition, prevention, and management; Int'l Journal of Trauma Nursing; ; vol. 1; No. 1; pp. 19-26; Jan. 1995.

(Continued)

*Primary Examiner* — Nicholas Lucchesi
*Assistant Examiner* — Gerald Landry, II
(74) *Attorney, Agent, or Firm* — Shay Glenn LLP (57) ABSTRACT

A method of providing hypothermia to a patient including the steps of inserting a fluid delivery member into a peritoneal cavity of the patient; delivering hypothermia fluid from a fluid source into the peritoneal cavity through the delivery member; and limiting fluid pressure within the peritoneal cavity without providing feedback control to the fluid source. The invention also provides an apparatus for practicing the method.

73 Claims, 11 Drawing Sheets

U.S. PATENT DOCUMENTS

| | | | |
|---|---|---|---|
| 4,963,130 A | 10/1990 | Osterholm | |
| 5,108,364 A | 4/1992 | Takezawa et al. | |
| 5,122,267 A | 6/1992 | Giovanetti et al. | |
| 5,141,492 A | 8/1992 | Dadson et al. | |
| 5,141,493 A | 8/1992 | Jacobsen et al. | |
| 5,149,321 A | 9/1992 | Klatz et al. | |
| 5,245,367 A | 9/1993 | Miller et al. | |
| 5,249,585 A | 10/1993 | Turner et al. | |
| 5,261,891 A | 11/1993 | Brinkerhoff et al. | |
| 5,344,136 A | 9/1994 | Capdeboscq | |
| 5,354,277 A | 10/1994 | Guzman et al. | |
| 5,380,160 A | 1/1995 | Chen | |
| 5,478,329 A | 12/1995 | Ternamian | |
| 5,554,280 A | 9/1996 | Loehr | |
| 5,562,821 A | 10/1996 | Gutierrez-Collazo | |
| 5,623,940 A | 4/1997 | Daikuzono | |
| 5,665,227 A | 9/1997 | Watt | |
| 5,693,017 A | 12/1997 | Spears et al. | |
| 5,709,654 A | 1/1998 | Klatz et al. | |
| 5,709,661 A | 1/1998 | Van Egmond et al. | |
| 5,730,720 A | 3/1998 | Sites et al. | |
| 5,752,929 A | 5/1998 | Klatz et al. | |
| 5,755,756 A * | 5/1998 | Freedman et al. | 607/110 |
| 5,837,003 A | 11/1998 | Ginsburg | |
| 5,916,153 A | 6/1999 | Rhea, Jr. | |
| 6,019,729 A | 2/2000 | Itoigawa et al. | |
| 6,019,783 A | 2/2000 | Philips et al. | |
| 6,066,163 A | 5/2000 | John | |
| 6,117,076 A | 9/2000 | Cassidy | |
| 6,126,684 A | 10/2000 | Gobin et al. | |
| 6,146,411 A | 11/2000 | Noda et al. | |
| 6,149,624 A | 11/2000 | McShane | |
| 6,149,670 A | 11/2000 | Worthen et al. | |
| 6,165,207 A | 12/2000 | Balding et al. | |
| 6,175,688 B1 | 1/2001 | Cassidy et al. | |
| 6,188,930 B1 | 2/2001 | Carson | |
| 6,197,045 B1 | 3/2001 | Carson | |
| 6,231,594 B1 | 5/2001 | Dae | |
| 6,254,567 B1 | 7/2001 | Treu et al. | |
| 6,261,312 B1 | 7/2001 | Dobak, III et al. | |
| 6,264,680 B1 | 7/2001 | Ash | |
| 6,287,326 B1 | 9/2001 | Pecor | |
| 6,290,717 B1 | 9/2001 | Philips | |
| 6,299,599 B1 | 10/2001 | Pham et al. | |
| 6,304,776 B1 | 10/2001 | Muntermann | |
| 6,312,452 B1 | 11/2001 | Dobak, III et al. | |
| 6,336,910 B1 | 1/2002 | Ohta et al. | |
| 6,338,727 B1 | 1/2002 | Noda et al. | |
| 6,368,304 B1 | 4/2002 | Aliberto et al. | |
| 6,375,674 B1 | 4/2002 | Carson | |
| 6,379,331 B2 | 4/2002 | Barbut et al. | |
| 6,405,080 B1 | 6/2002 | Lasersohn et al. | |
| 6,409,699 B1 * | 6/2002 | Ash | 604/29 |
| 6,419,643 B1 | 7/2002 | Shimada et al. | |
| 6,436,295 B2 | 8/2002 | Kim | |
| 6,447,474 B1 | 9/2002 | Balding | |
| 6,450,990 B1 | 9/2002 | Walker et al. | |
| 6,451,045 B1 | 9/2002 | Walker et al. | |
| 6,458,150 B1 | 10/2002 | Evans et al. | |
| 6,460,544 B1 | 10/2002 | Worthen | |
| 6,461,379 B1 | 10/2002 | Carson et al. | |
| 6,480,257 B2 | 11/2002 | Cassidy et al. | |
| 6,497,721 B2 | 12/2002 | Ginsburg et al. | |
| 6,520,933 B1 | 2/2003 | Evans et al. | |
| 6,529,775 B2 | 3/2003 | Whitebook et al. | |
| 6,530,945 B1 | 3/2003 | Noda et al. | |
| 6,530,946 B1 | 3/2003 | Noda et al. | |
| 6,547,811 B1 * | 4/2003 | Becker et al. | 607/105 |
| 6,551,302 B1 | 4/2003 | Rosinko et al. | |
| 6,554,797 B1 | 4/2003 | Worthen | |
| 6,572,640 B1 | 6/2003 | Balding et al. | |
| 6,579,496 B1 | 6/2003 | Fausset et al. | |
| 6,581,403 B2 | 6/2003 | Whitebook et al. | |
| 6,582,398 B1 | 6/2003 | Worthen et al. | |
| 6,585,692 B1 | 7/2003 | Worthen | |
| 6,592,577 B2 | 7/2003 | Abboud et al. | |
| 6,592,612 B1 | 7/2003 | Samson et al. | |
| 6,602,243 B2 | 8/2003 | Noda | |
| 6,620,187 B2 | 9/2003 | Carson et al. | |
| 6,620,189 B1 | 9/2003 | Machold et al. | |
| 6,635,053 B1 | 10/2003 | Lalonde et al. | |
| 6,641,602 B2 | 11/2003 | Balding | |
| 6,641,603 B2 | 11/2003 | Walker et al. | |
| 6,645,232 B2 | 11/2003 | Carson | |
| 6,645,234 B2 | 11/2003 | Evans et al. | |
| 6,648,905 B2 | 11/2003 | Hoglund et al. | |
| 6,660,027 B2 | 12/2003 | Gruszecki et al. | |
| 6,669,715 B2 | 12/2003 | Hoglund et al. | |
| 6,673,098 B1 | 1/2004 | Machold et al. | |
| 6,676,409 B2 | 1/2004 | Grant | |
| 6,676,689 B2 | 1/2004 | Dobak, III et al. | |
| 6,682,551 B1 | 1/2004 | Worthen et al. | |
| 6,685,733 B1 | 2/2004 | Dae et al. | |
| 6,692,518 B2 | 2/2004 | Carson | |
| 6,692,519 B1 | 2/2004 | Hayes, Jr. | |
| 6,695,873 B2 | 2/2004 | Dobak, III et al. | |
| 6,695,874 B2 | 2/2004 | Machold et al. | |
| 6,699,267 B2 | 3/2004 | Voorhees et al. | |
| 6,699,268 B2 | 3/2004 | Kordis et al. | |
| 6,702,842 B2 | 3/2004 | Dobak, III et al. | |
| 6,704,590 B2 | 3/2004 | Haldeman | |
| 6,706,060 B2 | 3/2004 | Tzeng et al. | |
| 6,709,448 B2 | 3/2004 | Walker et al. | |
| 6,716,236 B1 | 4/2004 | Tzeng et al. | |
| 6,719,724 B1 | 4/2004 | Walker et al. | |
| 6,733,517 B1 | 5/2004 | Collins | |
| 6,740,109 B2 | 5/2004 | Dobak, III | |
| 6,743,218 B2 | 6/2004 | Maginot et al. | |
| 6,746,474 B2 | 6/2004 | Saadat | |
| 6,749,625 B2 | 6/2004 | Pompa et al. | |
| 6,752,786 B2 | 6/2004 | Callister | |
| 6,764,391 B1 | 7/2004 | Grant et al. | |
| 6,796,995 B2 | 9/2004 | Pham et al. | |
| 6,799,063 B2 | 9/2004 | Carson | |
| 6,800,068 B1 | 10/2004 | Dae et al. | |
| 6,802,855 B2 | 10/2004 | Ellingboe et al. | |
| 6,807,444 B2 | 10/2004 | Tu et al. | |
| 6,811,551 B2 | 11/2004 | Dae et al. | |
| 6,818,012 B2 | 11/2004 | Ellingboe | |
| 6,819,950 B2 | 11/2004 | Mills | |
| 6,827,728 B2 | 12/2004 | Ellingboe et al. | |
| 6,827,898 B1 | 12/2004 | Fausset et al. | |
| 6,872,222 B2 | 3/2005 | Luo et al. | |
| 6,878,156 B1 | 4/2005 | Noda | |
| 6,887,262 B2 | 5/2005 | Dobak, III et al. | |
| 6,887,263 B2 | 5/2005 | Bleam et al. | |
| 6,893,454 B2 | 5/2005 | Collins | |
| 6,921,198 B2 | 7/2005 | Gruszecki et al. | |
| 6,974,463 B2 | 12/2005 | Magers et al. | |
| 6,981,945 B1 | 1/2006 | Sarvazyal et al. | |
| 7,001,418 B2 | 2/2006 | Noda | |
| 7,008,444 B2 | 3/2006 | Dae et al. | |
| 7,018,399 B2 | 3/2006 | Dobak, III et al. | |
| 7,063,718 B2 | 6/2006 | Dobak, III | |
| 7,070,612 B1 | 7/2006 | Collins et al. | |
| 7,077,825 B1 | 7/2006 | Stull | |
| 7,090,792 B1 | 8/2006 | Balding et al. | |
| 7,097,657 B2 | 8/2006 | Noda et al. | |
| 7,144,407 B1 | 12/2006 | Lasersohn | |
| 7,172,586 B1 | 2/2007 | Dae et al. | |
| 7,181,927 B2 | 2/2007 | Collins et al. | |
| 7,255,709 B2 | 8/2007 | Walker et al. | |
| 7,264,680 B2 | 9/2007 | Gebhart et al. | |
| 7,276,046 B1 | 10/2007 | Suzuki et al. | |
| 7,278,984 B2 | 10/2007 | Noda et al. | |
| 7,287,398 B2 | 10/2007 | Noda et al. | |
| 7,294,142 B2 | 11/2007 | Dobak, III et al. | |
| 7,300,453 B2 | 11/2007 | Yon | |
| 7,311,724 B1 | 12/2007 | Ginsburg | |
| 7,311,725 B2 | 12/2007 | Dobak, III | |
| 7,361,186 B2 | 4/2008 | Voorhees et al. | |
| 7,371,254 B2 | 5/2008 | Dobak, III | |
| 7,407,487 B2 | 8/2008 | Dae et al. | |
| 7,425,216 B2 | 9/2008 | Collins | |
| 7,458,984 B2 | 12/2008 | Yon et al. | |
| 7,491,223 B2 | 2/2009 | Lasheras | |
| 7,566,341 B2 | 7/2009 | Keller et al. | |

| | | | | | | |
|---|---|---|---|---|---|---|
| 7,640,768 B2 | 1/2010 | Noda et al. | | JP | 2005-528160 | 9/2005 |
| 7,666,213 B2 | 2/2010 | Freedman, Jr. et al. | | JP | 2005527331 A | 9/2005 |
| 7,666,215 B2 | 2/2010 | Callister et al. | | JP | 2005536277 | 12/2005 |
| 7,713,241 B2 | 5/2010 | Cartledge et al. | | KR | 100378358 B1 | 5/2003 |
| 7,771,460 B2 | 8/2010 | Ginsburg et al. | | WO | WO 93/13718 A1 | 7/1993 |
| 7,819,835 B2 | 10/2010 | Landy et al. | | WO | WO 98/04191 A1 | 2/1998 |
| 7,824,436 B2 | 11/2010 | Barbut et al. | | WO | WO 99/65552 A1 | 12/1999 |
| 7,827,005 B2 | 11/2010 | Kimball | | WO | WO 00/48670 A1 | 8/2000 |
| 2001/0035046 A1 | 11/2001 | Williams | | WO | WO 00/72779 A2 | 12/2000 |
| 2002/0026094 A1 | 2/2002 | Roth | | WO | WO 01/03606 A2 | 1/2001 |
| 2002/0033181 A1 | 3/2002 | Groth et al. | | WO | WO 01/17471 A1 | 3/2001 |
| 2002/0147481 A1* | 10/2002 | Brugger et al. ............... 607/106 | | WO | WO 01/39819 A2 | 6/2001 |
| 2003/0018279 A1 | 1/2003 | Rosenblatt | | WO | WO 01/41708 A2 | 6/2001 |
| 2003/0131844 A1 | 7/2003 | Kumar et al. | | WO | WO 01/58509 A1 | 8/2001 |
| 2003/0135087 A1 | 7/2003 | Hickle et al. | | WO | WO 02/26175 A1 | 4/2002 |
| 2004/0087606 A1 | 5/2004 | Voorhees et al. | | WO | WO 02/26176 A1 | 4/2002 |
| 2004/0102826 A1 | 5/2004 | Lasheras et al. | | WO | WO 02/26285 A2 | 4/2002 |
| 2004/0122353 A1 | 6/2004 | Shahmirian et al. | | WO | WO 02/26307 A1 | 4/2002 |
| 2004/0138701 A1 | 7/2004 | Haluck | | WO | WO 02/058606 A1 | 8/2002 |
| 2004/0158119 A1 | 8/2004 | Osorio et al. | | WO | WO 03/005908 A2 | 1/2003 |
| 2004/0172116 A1 | 9/2004 | Seifert et al. | | WO | WO 03/059218 A1 | 7/2003 |
| 2004/0193098 A1 | 9/2004 | Wentling et al. | | WO | WO 2006/060514 A1 | 6/2006 |
| 2004/0231664 A1 | 11/2004 | Lurie et al. | | WO | WO 2009/071094 A2 | 6/2009 |
| 2005/0033391 A1 | 2/2005 | Worthen et al. | | WO | WO 2009/071096 A2 | 6/2009 |
| 2005/0172212 A1 | 8/2005 | Birsa et al. | | WO | WO 2009/071097 A1 | 6/2009 |
| 2005/0177212 A1 | 8/2005 | Njemanze | | WO | WO 2009/071098 A2 | 6/2009 |
| 2005/0203598 A1* | 9/2005 | Becker et al. ................. 607/105 | | WO | WO 2009071095 A2 | 6/2009 |
| 2006/0025839 A1* | 2/2006 | Gonzales ....................... 607/105 | | | | |
| 2006/0064146 A1 | 3/2006 | Collins | | | | |
| 2006/0161107 A1* | 7/2006 | Mantle .......................... 604/113 | | | | |
| 2006/0190066 A1 | 8/2006 | Worthen | | | | |
| 2006/0276864 A1 | 12/2006 | Collins | | | | |
| 2006/0293734 A1* | 12/2006 | Scott et al. .................... 607/105 | | | | |
| 2007/0027393 A1 | 2/2007 | Williams et al. | | | | |
| 2007/0045188 A1 | 3/2007 | Blanton | | | | |
| 2007/0051409 A1 | 3/2007 | Landy, III et al. | | | | |
| 2007/0106247 A1* | 5/2007 | Burnett et al. ................. 604/508 | | | | |
| 2007/0173755 A1 | 7/2007 | Alimi et al. | | | | |
| 2007/0203552 A1 | 8/2007 | Machold et al. | | | | |
| 2007/0225781 A1 | 9/2007 | Saadat et al. | | | | |
| 2008/0045867 A1 | 2/2008 | Jensen et al. | | | | |
| 2008/0077088 A1 | 3/2008 | Collins | | | | |
| 2008/0077206 A1 | 3/2008 | Collins | | | | |
| 2008/0119757 A1 | 5/2008 | Winter | | | | |
| 2008/0119788 A1 | 5/2008 | Winter | | | | |
| 2008/0154197 A1 | 6/2008 | Derrico et al. | | | | |
| 2008/0200863 A1 | 8/2008 | Chomas et al. | | | | |
| 2008/0234619 A1 | 9/2008 | Fausset et al. | | | | |
| 2008/0255644 A1 | 10/2008 | Carson | | | | |
| 2009/0099629 A1 | 4/2009 | Carson et al. | | | | |
| 2009/0124937 A1 | 5/2009 | Parks | | | | |
| 2009/0131835 A1 | 5/2009 | Voorhees et al. | | | | |
| 2009/0240312 A1* | 9/2009 | Koewler ........................ 607/104 | | | | |
| 2009/0312676 A1* | 12/2009 | Rousso et al. ................. 601/15 | | | | |
| 2010/0305656 A1 | 12/2010 | Imran et al. | | | | |

FOREIGN PATENT DOCUMENTS

| | | |
|---|---|---|
| JP | H05-038327 A | 2/1993 |
| JP | 07-275358 A | 10/1995 |
| JP | H08-508176 A | 9/1996 |
| JP | 09-108340 A | 4/1997 |
| JP | 2001-029459 A | 2/2001 |
| JP | 2001-87392 | 4/2001 |
| JP | 3387602 | 3/2003 |
| JP | 2003533243 | 11/2003 |
| JP | 2004-329763 A | 11/2004 |
| JP | 2004538087 A | 12/2004 |
| JP | 2005211652 | 8/2005 |

OTHER PUBLICATIONS

Mantle, Ross E.; U.S. Appl. No. 12/916,076 entitled "Device for the extravascular recirculation of fluid in body cavities," filed Oct. 29, 2010.

Burnett et al.; U.S. Appl. No. 12/615,045 entitled "Devices and Methods for Monitoring Core Temperature and an Intraperitoneal Parameter," filed Nov. 9, 2009.

Hall et al.; U.S. Appl. No. 12/702,165 entitled "Method and Apparatus for Inducing Therapeutic Hypothermia," filed Feb. 8, 2010.

Polderman et al.; Effects of therapeutic hypothermia on intracranial pressure and outcome in patients with severe head injury; Intensive Care Med; vol. 28; pp. 1563-1573; 2002.

Demling et al.; Initial management of burn patient; (from Burnsurgery.org); 2004.

Rutherford et al.; Management of the patient with an open abdomen: techniques in temporary and definitive closure; Curr Probl Surg; vol. 41; pp. 821-876; 2004.

Sieh et al.; Intra-abdominal hypertension and abdominal compartment syndrome; Langenbeck's Arch Surg; vol. 386; pp. 53-61; 2001.

Hwang et al.; Peri-operative concerns in thoracic trauma; Bailliére's Clinical Anaesthesiology; vol. 10; No. 1; pp. 123-153; 1996.

Stover et al.; Treating intracranial hypertension in patients with severe traumatic brain injury during neurointensive care; European Journal of Trauma; 2005(4); pp. 308-330; 2005.

Burnett et al.; U.S. Appl. No. 12/098,355 entitled "Device and method for safe access to a body cavity," filed Apr. 4, 2008.

Burnett et al.; U.S. Appl. No. 12/098,365 entitled "Automated therapy system and method," filed Apr. 4, 2008.

Davison et al.; Epidural cooling for regional spinal cord hypothermia during thoracoabdominal aneurysm repair; J. Vasc. Surg.; vol. 20(2); No. 304-10; Aug. 1994 (Abstract Only).

Hall et al.; U.S. Appl. No. 13/275,189 entitled "Method and Apparatus for Inducing Therapeutic Hypothermia," filed Oct. 17, 2011.

Burnett et al.; U.S. Appl. No. 13/354,210 entitled "Automated Therapy System and Method," filed Jan. 19, 2012.

* cited by examiner

HYPOTHERMIA DEVICES AND METHODS

CROSS REFERENCE TO RELATED APPLICATIONS

This application claims priority under 35 U.S.C. §119 to U.S. Patent Application No. 60/958,717, filed Jul. 9, 2007, the disclosure of which is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Hypothermia has been shown to provide distinct medical benefits to myocardial infarction, traumatic brain injury, stroke, cardiac arrest and other patients by limiting the size of the infarction and related tissue injury if initiated soon enough and if the level of cooling is significant enough. Both of these limitations—initiation of and depth of cooling—have made practical application of the technology quite challenging, particularly in an ambulance or other emergency settings in the field. Initiation of cooling, for example, is a major issue since most technologies require sophisticated machinery that would be difficult to place in ambulance, so the patient, at best, receives the hypothermic benefit some time after they reach the hospital. Of the technologies that can be initiated in the field, such as cooling blankets, cooling caps, etc., the depth of cooling is a major issue due to surface area limitations, complications (such as intense shivering response) and patient access issues (once the blanket is on, it may be difficult to access the patient).

In addition to externally applied cooling, hypothermia may be induced by cooling the interior of the subject's body, such as by accessing the vasculature or an internal cavity. See, e.g., U.S. Pat. No. 5,752,929; U.S. Pat. No. 5,709,654 and US 2007/0106247.

SUMMARY OF THE INVENTION

The present invention relates to patient hypothermia systems and methods. Embodiments of the invention provide apparatus, systems and methods for achieving therapeutic hypothermia using minimally invasive access of the peritoneal cavity or other body cavity. Such embodiments can use minimally invasive methods to deliver and circulate hypothermic solutions to the peritoneal or other body cavity to reduce body temperature to a selected level for treatment of a number of medical conditions where there is diminished perfusion to one or more locations in the body. Such conditions can include various cardiac conditions including myocardial infarction and cardiac arrest; cerebral conditions including stroke and head trauma; and various hemorrhagic events due to arterial dissection or rupture or trauma. Particular hypothermic regimens (e.g., temperature and rate of cooling) can be employed to treat particular conditions e.g. stroke vs. myocardial infarction so as to reduce the amount of ischemic reperfusion injury to vital organs resulting from the particular ischemic event.

Also, some embodiments can have hypothermic regimens for various surgical procedures to reduce the amount of post-surgical inflammation and to provide a tissue protective effect so as to extend the operating times for procedures that require reduced perfusion at the surgical site or throughout the body. Examples of the latter application include open-heart procedures where the heart can be cooled to allow for longer periods during which the heart is arrested and neurosurgical procedures to provide a neuro-protective effect for tissue at or near the operative site.

Selection of a particular hypothermic regimen can be made by the user from a database of regimens stored in memory resources within a system control unit (e.g., a console) or otherwise electronically coupled to the system either directly or wirelessly. In particular embodiments, the hypothermic regimen can be stored in a flash memory or other non-volatile memory device coupled to a disposable catheter set or kit used by the system. The memory device could then interface and upload the regimen to the control device, for example a docking station that the flash memory device plugs in to RF and other wireless interfaces to the system control device using BLUE TOOTH or another protocol are also contemplated.

These and related embodiments can also be utilized for patient resuscitation from various ischemic, hemorrhagic events (e.g., stroke or cardiac arrest) as well as shock through the use of peritoneal therapeutic solutions to oxygenate ischemic tissue, reduce reperfusion injury, and increase blood pressure by exerting a compressive force against the peritoneal or other body cavity vasculature. Such therapeutic solutions can include various peritoneal dialysis solutions which can comprise nutrients and one or more reperfusion injury protective agents. Also, the solution can comprise oxygenated solutions such as oxygenated fluorocarbon solutions that can be configured to deliver sufficient oxygen to tissue (by gas exchange with peritoneal or other surrounding tissue) to at least partially meet the oxygen demands of the body. For embodiments of the invention used to treat shock, the solution need not be chilled and can actually be warmed.

Also, many embodiments of the invention can be configured as a portable body cavity infusion/hypothermic system that can be readily transported in an ambulance, carried and used at a trauma scene by EMT's, military medics and emergency room personnel. Thus, one or more components of the system can include a handle, or the entire system can be integrated into an assembly having a handle. Further, as described herein, embodiments of a portable system can be configured for ease of use so as to require minimal set up time and manual dexterity by medical personnel. For example, embodiments of the system can use a subcutaneous access device that uses a stop or other means to control the depth of penetration into subcutaneous tissue so that the user need not have to precisely position the access device. This access device can be used in conjunction with an infusion catheter having a sensor configured to alert the user when the catheter has entered the peritoneal cavity so as to minimize or eliminate the risk of injuring a peritoneal organ. The infusion catheter can make use of quick connections for rapid connection to liquid and gas sources, fluid collection devices and other system components. The subsequent infusion and thermal control of fluids can then be automated through use of a computer controller or other electronic controller. In use, such embodiments provide a system with a fast set up time, high degree of reproducibility, and requires minimal dexterity and training of medical personnel.

One aspect of the invention provides a method of providing hypothermia to a patient. The method includes the steps of inserting a fluid delivery member into a peritoneal cavity of the patient; delivering hypothermia fluid from a fluid source into the peritoneal cavity through the delivery member; and limiting fluid pressure within the peritoneal cavity without providing feedback control to the fluid source. In some embodiments, the limiting step includes the step of extracting fluid from the peritoneal cavity when the pressure reaches a predetermined pressure, such as, e.g., by opening a pressure relief valve at the predetermined pressure.

In embodiments in which the fluid source includes a pump, the limiting step can include the step of limiting pump outlet pressure such as, e.g., by limiting torque on a moving pump component. In embodiments in which the fluid source includes a fluid container, the step of limiting fluid pressure can include the step of limiting height of the container over the patient.

In some embodiments, the delivering step includes the step of commencing delivery of fluid through the delivery member automatically when an outlet port of the delivery member enters the peritoneal cavity. The method may also include the step of activating a heat exchange element within the peritoneal cavity and/or cooling the fluid in the cavity, such as by using an endothermic reaction or using a compressed gas. In some embodiments, the method includes the step of cycling a fixed volume of fluid into and out of the peritoneal cavity.

In some embodiments, the fluid includes a hypertonic ice slurry and a hypotonic cold fluid. The hypertonic ice slurry and a hypotonic cold fluid together may be isotonic.

The fluid delivery member may be inserted into the peritoneal or other cavity in different ways in different embodiments. For example, in some embodiments the inserting step includes the step of inserting the fluid delivery member transgastrically or transrectally.

In some embodiments, the method includes the step of measuring patient temperature in e.g., the patient's trachea, esophagus and/or bladder. The measured temperature may be used to control fluid flow and/or temperature.

In some embodiments, the method includes the step of providing automated circulation to the patient with a CPR machine. Some embodiments also include the step of contacting an exterior surface of the patient with a cooling blanket.

Another aspect of the invention provides a hypothermia system including: a fluid source; a fluid delivery member adapted to be inserted into a peritoneal cavity of a patient; and a cavity pressure limiter adapted to limit fluid pressure within the peritoneal cavity without providing feedback control to the fluid source. Some embodiments also include a fluid extraction member adapted to extract fluid from the peritoneal cavity. In some such embodiments, the cavity pressure limiter has a pressure relief valve controlling flow of fluid through the fluid extraction member. The fluid extraction member may also have a weight at an inlet port.

In some embodiments, the fluid source includes a pump and the cavity pressure limiter includes a torque limiter (such as a clutch plate) in the pump. The fluid delivery member may also include a multi-lumen trocar.

Some embodiments of the invention include a heat exchange element supported by the fluid delivery member. The fluid source may include a hypertonic ice slurry and a hypotonic cold fluid, combinations of which may be isotonic.

Embodiments of the invention may also include delivery tools for the fluid delivery member, such as a transgastric delivery tool or a transrectal delivery tool. Some embodiments may also include a patient temperature sensor mounted on an endotracheal cuff, an esophageal catheter and/or a bladder catheter.

Some embodiments may also have a CPR machine adapted to provided automated circulation to the patient and/or a cooling blanket.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Embodiments of the invention provide apparatus, systems and methods for providing therapeutic hypothermia through minimally invasive access to the peritoneal cavity. Many embodiments provide a system for providing hypothermia, resuscitation or other treatment in response to stroke, myocardial infarction, blood loss or any condition resulting in decreased perfusion to one or more locations in the body, including both internal organs and the extremities. Embodiments of the invention may also be used with cadavers to preserve organs for later transplant. The term "patient" may be used herein to denote either living subjects requiring hypothermia therapy or dead subjects whose organs need to be preserved for transplant.

Figure 1:
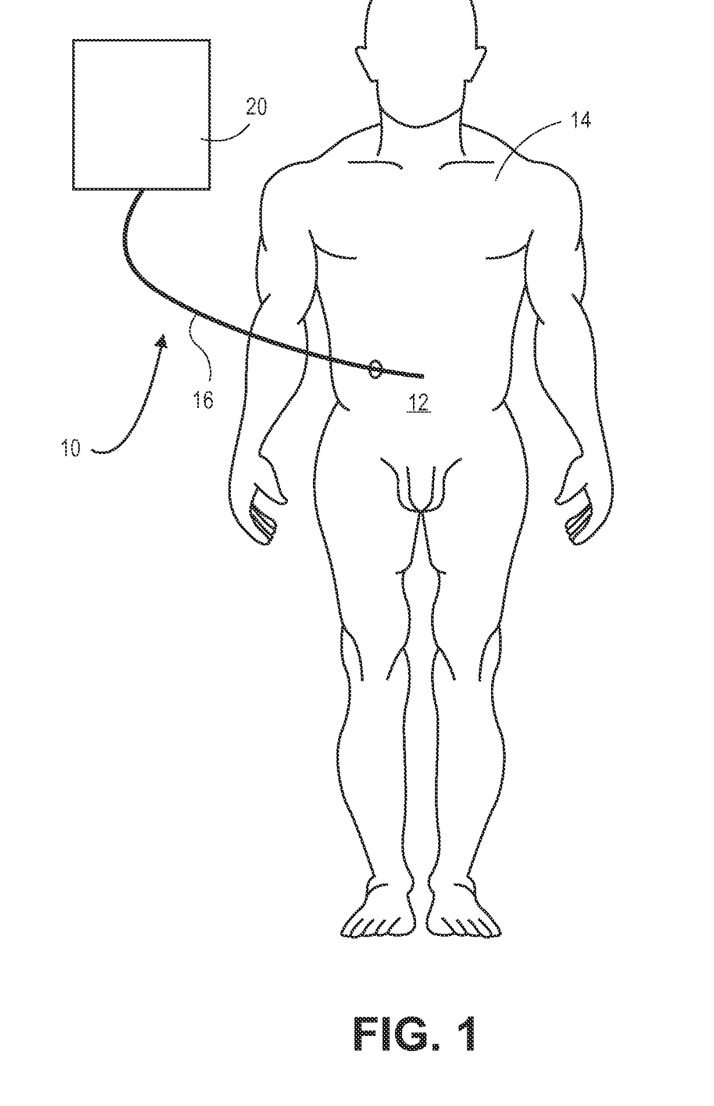
FIG. 1 shows a hypothermia therapy system according to certain embodiments of the invention.

FIG. 1 shows a system 10 for the delivery of hypothermic or other fluid from a fluid source 20 through a fluid delivery member 16 (including, e.g., a catheter) to a peritoneal or other tissue cavity 12 of a patient 14. In various embodiments, the delivered fluid comprises a solution for the delivery of a medical treatment such as hypothermic or resuscitative treatment. Suitable fluids can comprise various saline solutions (e.g., ringers lactate), various peritoneal dialysis fluids including nutritive based peritoneal dialysis fluid (e.g., those containing dextrose and other sugars), and fluorocarbon solutions configure for oxygen transport and artificial blood solutions known in the art. For aqueous embodiments, the solution can also include one or more freezing point depression compounds (e.g., NaCl) allowing the solution to be cooled below the freezing point of water to allow for faster cooling when so desired.

Also, the delivered fluid can contain one or more medicaments for treatment of myocardial infarction, cardiac arrest or other severe cardiac condition, stroke, shock, reperfusion injury or other medical conditions. Specific families of medicaments can include vasoconstrictors, hemolytic compounds (e.g., TPA, streptokinase and like compounds), anticoagulants, coagulants, calcium channel blockers, antibiotics, manitols. Also in specific embodiments, the delivered fluid can be configured to have resuscitative effects for treatment of heart attack, stroke, or severe blood loss. It can also have various agents known in the art for treatment of reperfusion injury. The delivered amount of a particular medicament can be titrated to the patient's weight and condition. Also, the dose of particular compounds can both be delivered as bolus with the initial bolus of hypothermic solution and also on a continuous basis. The delivery rate of a particular medicament or group of medicaments can also be controlled responsive to the patient's temperature, blood pressure, heart rate or other vital sign monitored manually, by system 10, or by other monitoring means.

The delivered fluid can also comprise oxygenated solutions such as supersaturated saline, oxygenated fluorocarbon solutions that can be configured to deliver sufficient oxygen to tissue (by gas exchange with peritoneal or other surrounding tissue) to at least partially meet the oxygen demands of the body. Fluorocarbon solutions can be pre-oxygenated or can be oxygenated in the fluid source 20 or outside of it using oxygen gas sources described herein. The delivered fluid can also include contrast media to allow for imaging by x-ray, MRI, ultrasound, and other imaging modalities known in the art.

A phase change solution, such as a slurry of ice, may be used within the cavity. Additives to the infusate may also be used to increase the cooling capacity of the fluid. One such additive is propylene glycol, but any safe compound may be used so long as it leads to greater cooling capacity. In some embodiments, a hypertonic ice slurry solution may be delivered to the patient's cavity followed by a hypotonic cold fluid with a net result of an isotonic fluid.

In various embodiments, such as some of those discussed below, the fluid source can include a patient cavity pressure limiter adapted to limit fluid pressure within the peritoneal or other cavity to which fluid delivery member 16 delivers fluid without providing feedback information or control to the fluid source. For example, in embodiments in which the fluid source is a bag of fluid suspended higher than the patient, the cavity pressure limiter could include a bag support (not shown) that limits the height of the bag over the patient cavity to which the fluid is being delivered. In embodiments in which the fluid source includes a pump, the cavity pressure limiter could include a controller controlling pump output pressure or a torque limiter (such as a clutch) limiting the output torque of a moving pump element. A high-flow, low-pressure pump may also be operated such that its output cannot exceed a predetermined pressure, such as, e.g., 10 cm $H_2O$.

When used to treat a patient, the fluid delivery member 16 is inserted into the patient's peritoneal cavity 12 or other cavity. A trocar or other suitable instrument may be used to aid insertion and sealing of the insertion site. In some embodiments, an insertion sensor such as described in U.S. patent application Ser. No. 12/098,355 may also be used. After insertion, hypothermia fluid is delivered from the fluid source 20 to the patient's cavity 12 through the delivery member. Fluid pressure within the cavity is limited without providing pressure feedback information or control to the fluid source.

Figure 2:
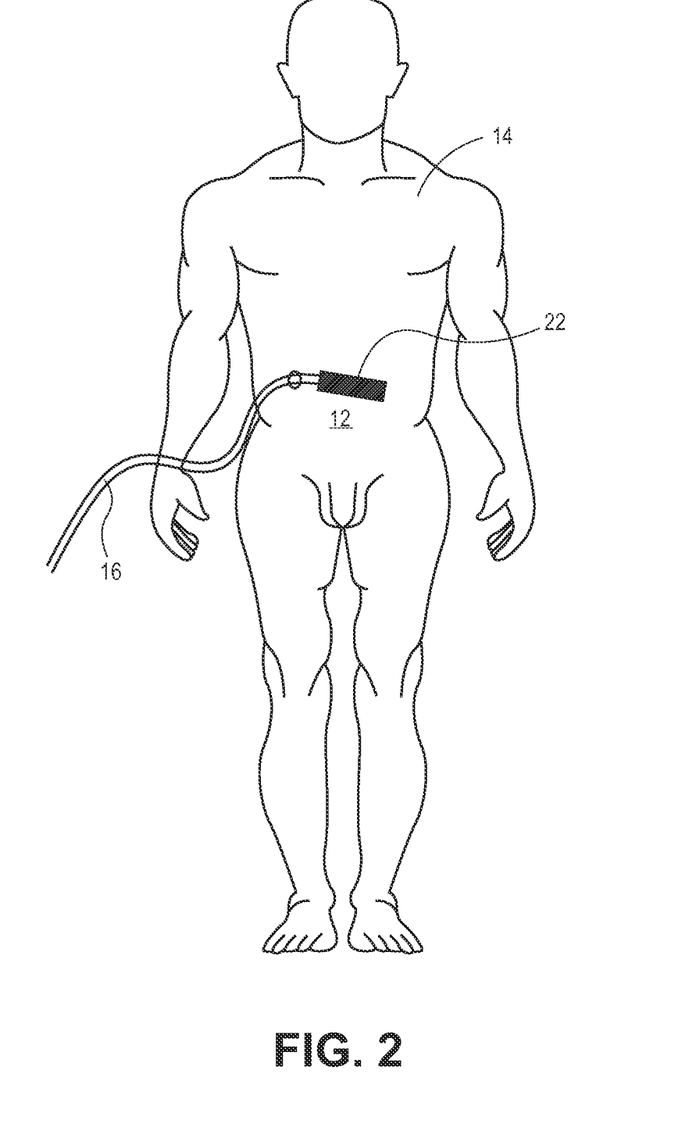
FIG. 2 shows a hypothermia therapy system according to another embodiment of the invention employing a heating/cooling element.

In another embodiment, the system may be used to infuse an initial bolus of fluid, or liquid/particulate mixture, but then may function as heat-exchanger to simply cool the fluid within the peritoneal cavity with no further fluid infusion and/or extraction required. For example, as shown in FIG. 2, the distal end of the fluid delivery member 16 has a cooling/warming element 22, such as a heat-exchanger. In this embodiment, the fluid may be left within the peritoneal cavity at the end of the cooling period or may be extracted. If the fluid is left in the cavity, it may be warmed by the heat-exchanger. Additionally, the fluid may be replaced by warmed fluid at the end of the cooling period and then warmed or cooled in order to achieve the desired rewarming rate. As an alternative, a heat-exchange catheter may be placed through or alongside the fluid delivery member within the cavity 12. In this embodiment, the catheter itself may contain a cooling/warming apparatus and/or a pumping mechanism to circulate fluid within the cavity without pumping the fluid externally. The cooling/warming apparatus may consist of a variety of mechanisms, including circulating fluid or gas, a peltier junction, etc.

In yet another embodiment, the fluid within the cavity may be cooled by an endothermic reaction which cools the peritoneal cavity via a chemical reaction. This reaction may be tailored to be temperature dependent and may be suspended or drastically slowed at the target temperature (typically within the 30-34 degree Celsius range). This reaction may also be generated within the fluid-filled cavity by a steady or intermittent infusion of reactive compounds which function to complete the endothermic reaction and lower the cavity temperature. Any endothermic chemical reaction may be used so long as it is biocompatible.

In yet another embodiment, instead of requiring the bag of fluid to be prechilled, it may be rapidly cooled using a $CO_2$ cartridge or other source of compressed gas or endothermic reaction to cool fluid immediately prior to its infusion into the cavity. In another version of this embodiment, the fluid may be cooled as it enters into the cavity and may be kept at room temperature outside of the body. This relieves the requirement for prechilling and decreases the overall nursing burden.

In yet another embodiment of the invention, a fixed volume of fluid may be used that is safe for all patients (i.e., 1-2 L) and is then automatically cycled to achieve the desired cooling/warming rates, based, e.g., on the temperature of the fluid in the cavity and additional temperature sensors elsewhere in the body. In this embodiment, the volume of fluid in the cavity can be kept track of by the pump and fluid infusion/extraction may be coupled to ensure that excessive pressures are not generated and excessive volumes are not infused. Alternatively, a fixed volume of fluid may be infused and the pressure measured post-infusion. This post-infusion pressure may be maintained throughout the treatment cycle to ensure that a minimum volume of fluid is maintained within the cavity.

Figure 3:
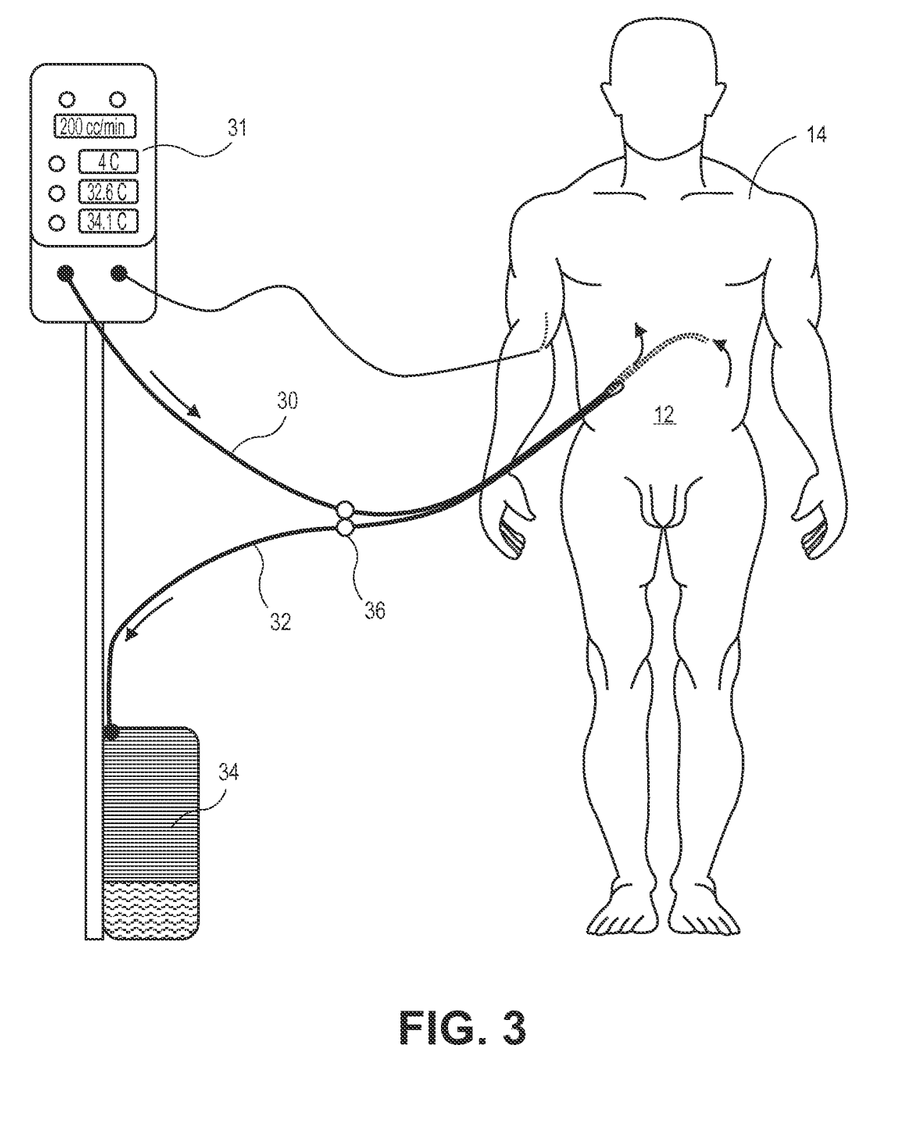
FIG. 3 shows a hypothermia therapy system according to an embodiment of the invention employing an infusion pump and a pressure-responsive valve.

In the embodiment shown in FIG. 3, the fluid delivery member includes a fluid infusion line 30 leading from the fluid source 31, which is shown here as an infusion pump. The system also includes a fluid extraction line 32 leading from the patient's peritoneal cavity 12 to a drainage reservoir 34. A pressure-responsive valve 36 (such as a pop-off valve or passive or active check valve), or other pressure limiting mechanism, may be incorporated in line with the infusion and extraction lumens to ensure that once the desired pressure is achieved the infused fluid is shunted back into the fluid path (or into the drainage reservoir) and/or the fluid extracted is immediately shunted outside of the body regardless of pump function. With these redundant safeguards, excessive cavity pressure may be prevented without halting further fluid influx and/or shunting fluid out of the peritoneal cavity. In this embodiment, these pop-off valves may be present on the inflow lumen, the outflow lumen, or both lumens. The pop-off valves may be the only safeguard against over-pressurization, or they may be used in combination with a pressure sensor as a redundant protection mechanism to ensure that the over-pressurization never occurs. The device may be capable of performing a diagnostic to check the functionality of both pop-off valves prior to therapy initiation.

Figure 4:
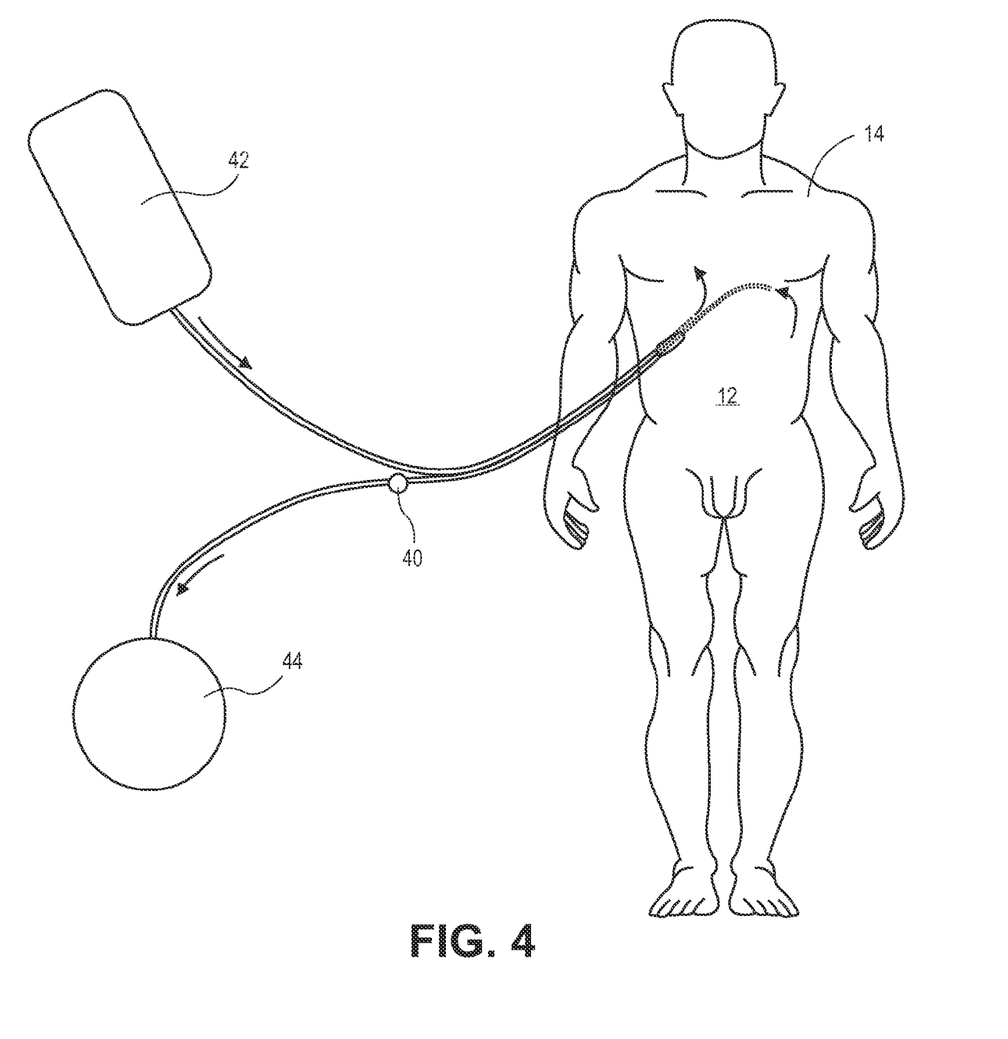
FIG. 4 shows a hypothermia therapy system according to another embodiment of the invention employing a pressure-responsive valve.

In the embodiment shown in FIG. 4, a pop-off valve 40 has been incorporated into a paramedic unit wherein the fluid source is a fixed volume bag 42. This system may be utilized in an ambulance, and the entire bag may be infused in every patient with the excess fluid being shunted directly to a waste reservoir 44 if the target or threshold pressure is exceeded. This will allow each patient to receive a maximum volume of fluid in transit, after which the infusion/extraction ports may be connected to the full device in the emergency room (or elsewhere), and the cycling of fluid and monitoring of temperatures and/or pressures may begin. The paramedic unit therefore needs to consist only of the infusion catheter 46, the safety pop-off valve 40 (or other pressure protective mechanism) and a reservoir of fluid 42 (pre-chilled or chilled on demand).

Figure 5:
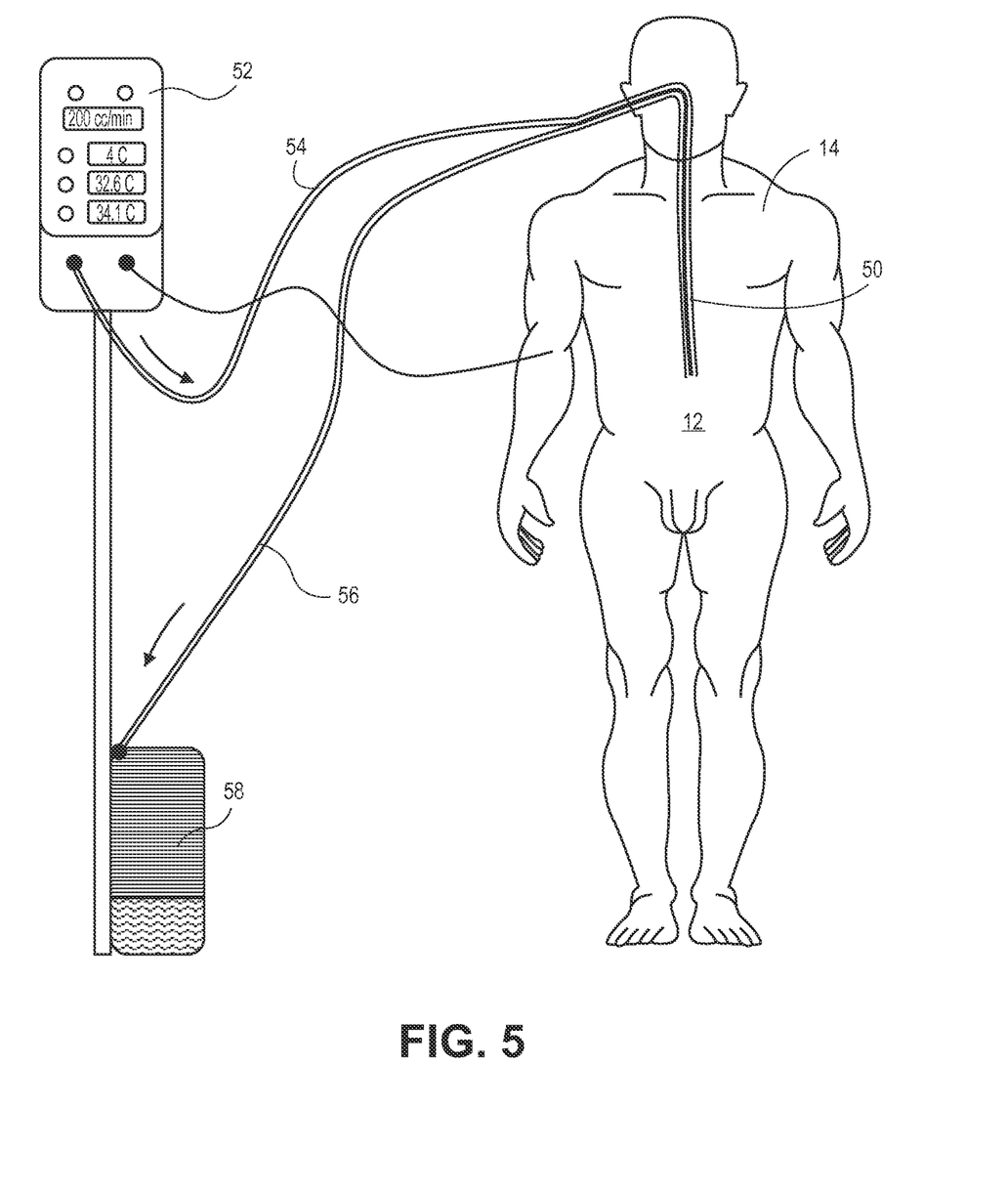
FIG. 5 shows a hypothermia therapy system according to an embodiment of the invention employing transgastric access to a patient cavity.

In many of the embodiments described above, the fluid delivery member accesses the patient's peritoneal cavity via an incision in the abdominal wall. Other means of accessing the peritoneal cavity are within the scope of the invention. For example, in the embodiment shown in FIG. 5, the fluid delivery member 50 accesses the peritoneal cavity transgastrically to deliver fluid from infusion pump (or other fluid source) 52 via catheter 54 and to (optionally) extract fluid through extraction line 56 to drainage reservoir 58. Other embodiments may employ transrectal access or other natural orifice translumenal access to the peritoneal cavity.

Figure 6:
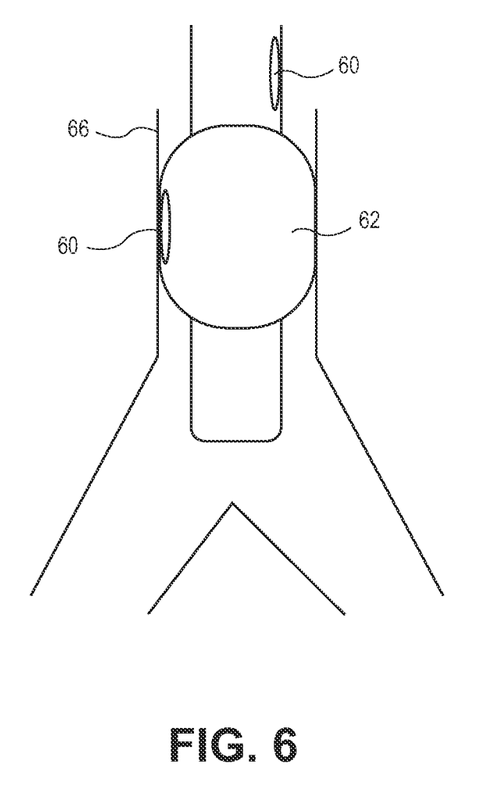
FIG. 6 shows temperature sensors on an endotracheal tube for use with a hypothermia therapy system according to embodiments of the invention.

In some embodiments it may be desirable to monitor the patient's temperature. For example, exhaled air may be used as an indication of core temperature. As shown in FIG. 6, temperature sensors 60 disposed on an endotracheal tube 61 (e.g., on the cuff 62 and/or on an interior surface of the lumen 64) may be placed within the patient's trachea 66 to measure the temperature of exhaled air to indicate the temperature of the lungs without requiring any invasive sensors. One or more temperature sensors may also be disposed in the airway line external to the patient. This information may be used to monitor or control warming or cooling of the patient. Also, the difference between inhaled and exhaled air can be correlated to patient core temperature. If an endotracheal tube is not being used, temperature sensors may also be disposed in a mask over the patient's nose and/or mouth.

Figure 7:
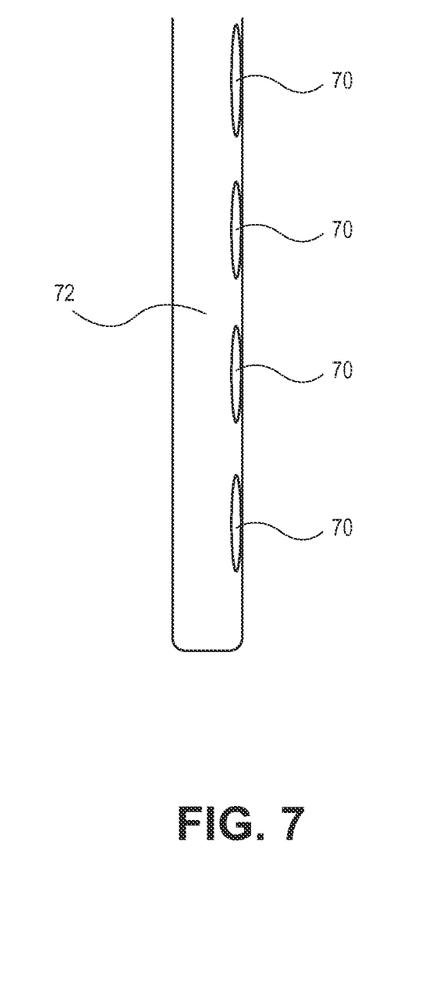
FIG. 7 shows temperature sensors on an esophageal catheter for use with a hypothermia therapy system according to embodiments of the invention.

FIG. 7 shows an alternative temperature sensor for use with the system of this invention. In this embodiment, multiple temperature sensors 70 are disposed along an esophageal catheter 72 for monitoring and/or control of the system. The use of multiple temperature sensors can help ensure that system control will not be based on an erroneous reading from a single under- or over-inserted sensor. Failure of one temperature sensor to agree with the others indicates that the sensor is in the wrong place.

Figure 8:
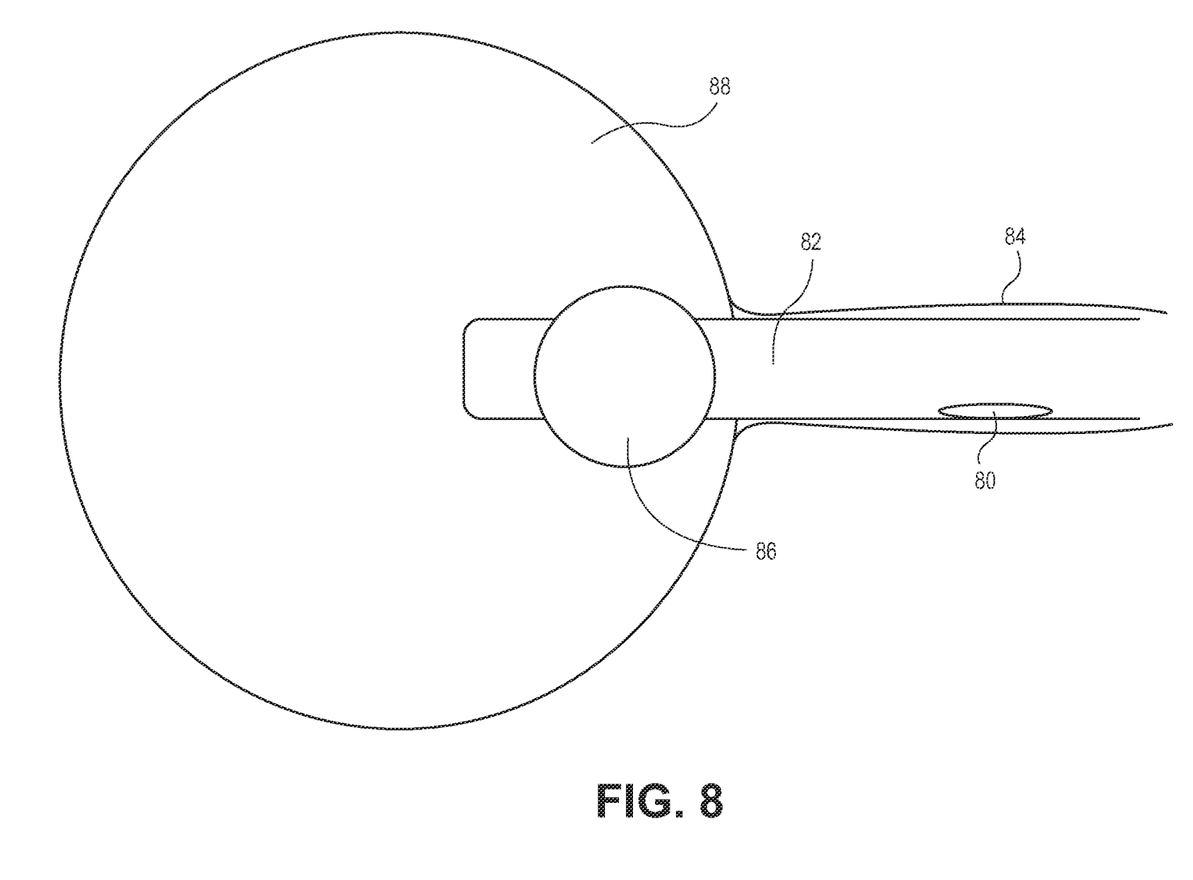
FIG. 8 shows a temperature sensor on a urethral catheter for use with a hypothermia therapy system according to embodiments of the invention.

FIG. 8 shows yet another temperature sensor for use with the system of this invention. In this embodiment, a temperature sensor 80 disposed on a urethral catheter 82 is placed within the urethra 84 as shown. A retention balloon 86 helps hold the catheter within the bladder 88 in a known manner. Once again, information from temperature sensor 80 may be used to monitor and/or control the warming or cooling provided by the system of the invention. Multiple temperature sensors may be used, as in the embodiment of FIG. 7.

Figure 9:
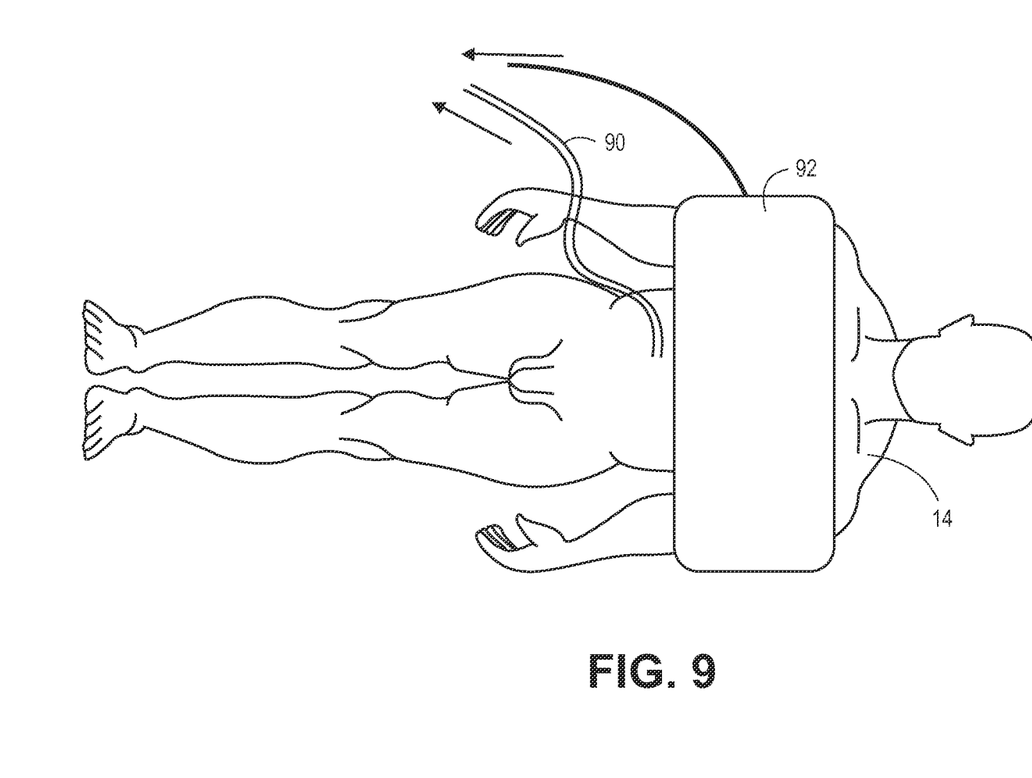
FIG. 9 shows a hypothermia system combined with a CPR resuscitation system according to an embodiment of the invention.

In some embodiments, the hypothermia system 90 may be combined with a CPR resuscitation system 92, as shown in FIG. 9. The two devices could, for example, share the same enclosure, battery and microprocessor and could function in unison to resuscitate the patient while providing therapeutic hypothermia.

Figure 10:
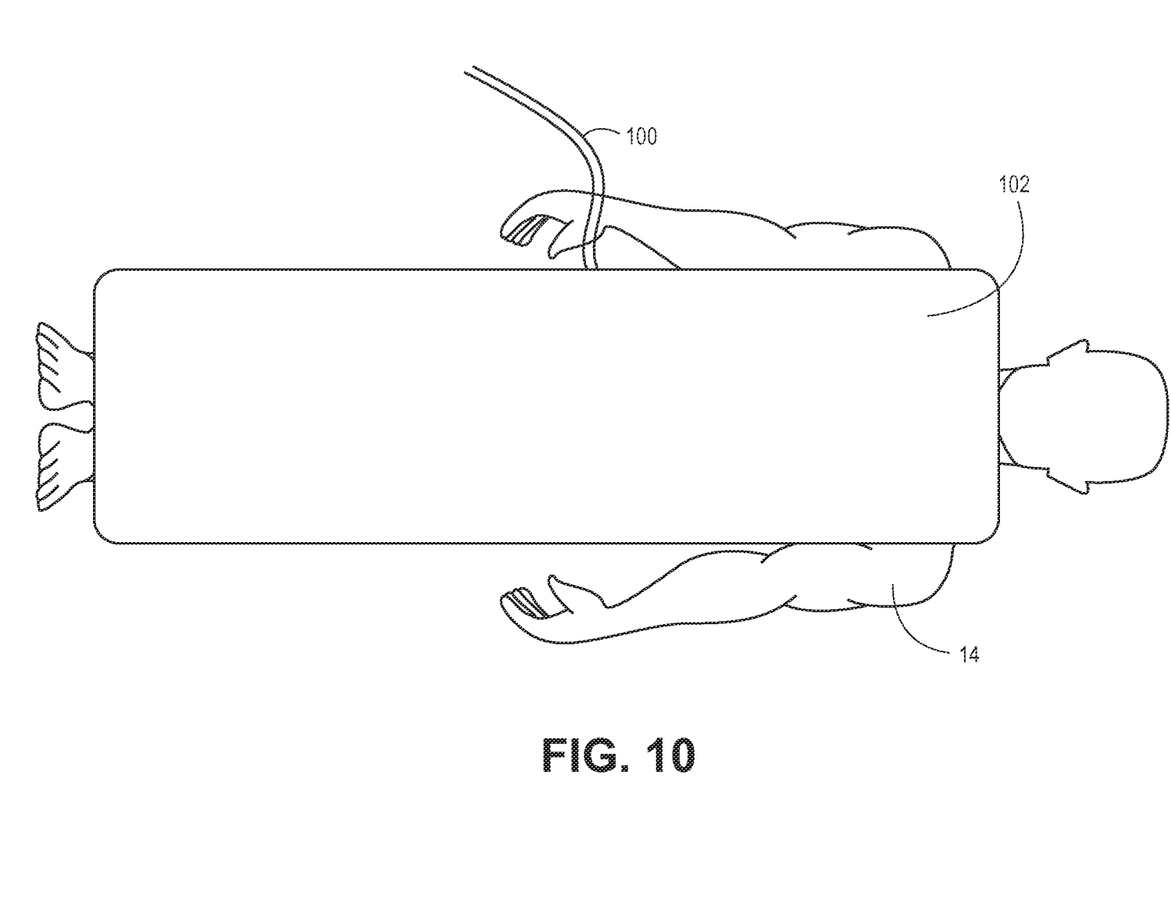
FIG. 10 shows a hypothermia system combined with an external cooling blanket according to an embodiment of the invention.

Additionally, the peritoneal infusion of cold or warm fluid could be used as an adjunct to other temperature management technologies. For example, 2 liters of cold fluid could be infused into the peritoneal cavity via a hypothermia system 100 in order to jump start the cooling process after which external cooling blankets 102 or other hypothermia producing therapies can be implemented, as shown in FIG. 10.

In yet further embodiments, the IV fluid may be cooled with an ultrasonic refrigeration method. Or the tissues may be cooled directly via ultrasonic or other energy transmission means. One such example involves the use of an ultra-sonic cooling incorporated into a helmet for a neuro-protective device. These focused cooling technologies may be used to target any organ, though, including the heart, brain, liver, kidneys, etc. or may be used to cool the entire body.

Tissue penetration and placement of the fluid delivery member can be achieved in any manner known in the art, such as that described in US 2007/0106247, which has been incorporated herein by reference. The device may then report entry to the user and/or automatically initiate therapy.

Figures 11, 12:
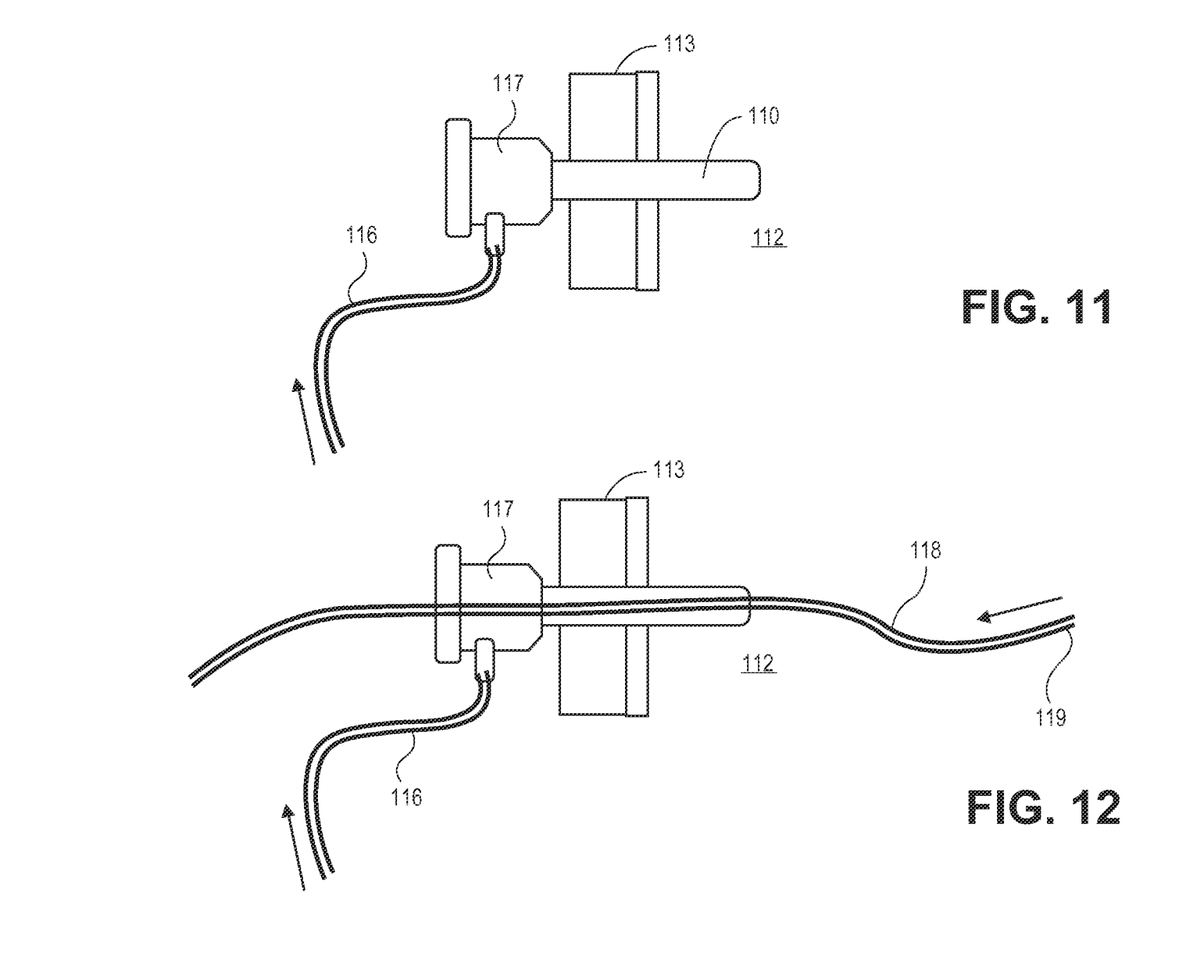
FIGS. 11 and 12 show an embodiment of the invention employing a trocar providing access for infusion and extraction lumens.

To provide lumens for fluid infusion and for fluid extraction, a dual lumen catheter may be used. FIGS. 11 and 12 show one embodiment in which initial access through the abdominal wall 113 to the cavity 112 is obtained with a fill trocar, catheter or needle 110. Infusion tubing 116 leads from a fluid source (not shown) to a cap or fluid seal 117. An extraction catheter 118 may be inserted through cap 117 to extract fluid from the cavity, e.g., after a rapid infusion phase of the therapy. In some embodiments, the distal end 119 and inlet port of the extraction catheter 118 may be weighted to ensure that it lies in the most dependent portion of the peritoneal cavity 112.

What is claimed is:

1. A method of providing hypothermia to a patient comprising:
   inserting a fluid delivery member into a peritoneal cavity of the patient;
   delivering hypothermia fluid from a fluid source into the peritoneal cavity through the delivery member; and
   limiting fluid pressure within the peritoneal cavity without providing feedback control to the fluid source by extracting fluid from the peritoneal cavity by opening a pressure relief valve when the pressure reaches a predetermined pressure.

2. The method of claim 1 wherein the fluid source comprises a fluid container, the step of limiting fluid pressure further comprising limiting a height of the container over the patient.

3. The method of claim 1 wherein the delivering step comprises commencing delivery of fluid through the delivery member automatically when an outlet port of the delivery member enters the peritoneal cavity.

4. The method of claim 1 further comprising activating a heat exchange element within the peritoneal cavity.

5. The method of claim 1 further comprising cooling the fluid in the cavity using an endothermic reaction.

6. The method of claim 1 further comprising cooling the fluid using a compressed gas.

7. The method of claim 1 further comprising cycling a fixed volume of fluid into and out of the peritoneal cavity.

8. The method of claim 1 wherein the fluid comprises a hypertonic ice slurry and a hypotonic cold fluid.

9. The method of claim 8 wherein the hypertonic ice slurry and a hypotonic cold fluid together are isotonic.

10. The method of claim 1 wherein the inserting step comprises inserting the fluid delivery member transgastrically.

11. The method of claim 1 wherein the inserting step comprises inserting the fluid delivery member transrectally.

12. The method of claim 1 further comprising measuring patient temperature.

13. The method of claim 12 wherein measuring patient temperature comprises measuring patient temperature in a trachea.

14. The method of claim 12 wherein measuring patient temperature comprises measuring patient temperature in an esophagus.

15. The method of claim 12 wherein measuring patient temperature comprises measuring patient temperature in a bladder.

16. The method of claim 1 further comprising providing automated circulation to the patient with a CPR machine.

17. The method of claim 1 further comprising contacting an exterior surface of the patient with a cooling blanket.

18. A method of providing hypothermia to a patient comprising:
inserting a fluid delivery member into a peritoneal cavity of the patient;
delivering hypothermia fluid with a pump from a fluid source into the peritoneal cavity through the delivery member; and
limiting fluid pressure within the peritoneal cavity without providing feedback control to the fluid source by limiting torque on a moving pump component.

19. The method of claim 18 wherein the fluid source comprises a fluid container, the step of limiting fluid pressure further comprising limiting a height of the container over the patient.

20. The method of claim 18 wherein the delivering step comprises commencing delivery of fluid through the delivery member automatically when an outlet port of the delivery member enters the peritoneal cavity.

21. The method of claim 18 further comprising activating a heat exchange element within the peritoneal cavity.

22. The method of claim 18 further comprising cooling the fluid in the cavity using an endothermic reaction.

23. The method of claim 18 further comprising cooling the fluid using a compressed gas.

24. The method of claim 18 further comprising cycling a fixed volume of fluid into and out of the peritoneal cavity.

25. The method of claim 18 wherein the fluid comprises a hypertonic ice slurry and a hypotonic cold fluid.

26. The method of claim 25 wherein the hypertonic ice slurry and a hypotonic cold fluid together are isotonic.

27. The method of claim 18 wherein the inserting step comprises inserting the fluid delivery member transgastrically.

28. The method of claim 18 wherein the inserting step comprises inserting the fluid delivery member transrectally.

29. The method of claim 18 further comprising measuring patient temperature.

30. The method of claim 29 wherein measuring patient temperature comprises measuring patient temperature in a trachea.

31. The method of claim 29 wherein measuring patient temperature comprises measuring patient temperature in an esophagus.

32. The method of claim 29 wherein measuring patient temperature comprises measuring patient temperature in a bladder.

33. The method of claim 18 further comprising providing automated circulation to the patient with a CPR machine.

34. The method of claim 18 further comprising contacting an exterior surface of the patient with a cooling blanket.

35. A method of providing hypothermia to a patient comprising:
inserting a fluid delivery member into a peritoneal cavity of the patient;
delivering hypothermia fluid from a fluid source into the peritoneal cavity through the delivery member;
measuring patient temperature in a trachea; and
limiting fluid pressure within the peritoneal cavity without providing feedback control to the fluid source.

36. The method of claim 35 wherein the fluid source comprises a fluid container, the step of limiting fluid pressure further comprising limiting a height of the container over the patient.

37. The method of claim 35 wherein the delivering step comprises commencing delivery of fluid through the delivery member automatically when an outlet port of the delivery member enters the peritoneal cavity.

38. The method of claim 35 further comprising activating a heat exchange element within the peritoneal cavity.

39. The method of claim 35 further comprising cooling the fluid in the cavity using an endothermic reaction.

40. The method of claim 35 further comprising cooling the fluid using a compressed gas.

41. The method of claim 35 further comprising cycling a fixed volume of fluid into and out of the peritoneal cavity.

42. The method of claim 35 wherein the fluid comprises a hypertonic ice slurry and a hypotonic cold fluid.

43. The method of claim 42 wherein the hypertonic ice slurry and a hypotonic cold fluid together are isotonic.

44. The method of claim 35 wherein the inserting step comprises inserting the fluid delivery member transgastrically.

45. The method of claim 35 wherein the inserting step comprises inserting the fluid delivery member transrectally.

46. The method of claim 35 further comprising providing automated circulation to the patient with a CPR machine.

47. The method of claim 35 further comprising contacting an exterior surface of the patient with a cooling blanket.

48. A method of providing hypothermia to a patient comprising:
inserting a fluid delivery member into a peritoneal cavity of the patient;
delivering hypothermia fluid from a fluid source into the peritoneal cavity through the delivery member;
measuring patient temperature in an esophagus; and
limiting fluid pressure within the peritoneal cavity without providing feedback control to the fluid source.

49. The method of claim 48 wherein the fluid source comprises a fluid container, the step of limiting fluid pressure further comprising limiting a height of the container over the patient.

50. The method of claim 48 wherein the delivering step comprises commencing delivery of fluid through the delivery member automatically when an outlet port of the delivery member enters the peritoneal cavity.

51. The method of claim 48 further comprising activating a heat exchange element within the peritoneal cavity.

52. The method of claim 48 further comprising cooling the fluid in the cavity using an endothermic reaction.

53. The method of claim 48 further comprising cooling the fluid using a compressed gas.

54. The method of claim 48 further comprising cycling a fixed volume of fluid into and out of the peritoneal cavity.

55. The method of claim 48 wherein the fluid comprises a hypertonic ice slurry and a hypotonic cold fluid.

56. The method of claim 55 wherein the hypertonic ice slurry and a hypotonic cold fluid together are isotonic.

57. The method of claim 48 wherein the inserting step comprises inserting the fluid delivery member transgastrically.

58. The method of claim 48 wherein the inserting step comprises inserting the fluid delivery member transrectally.

59. The method of claim 48 further comprising providing automated circulation to the patient with a CPR machine.

60. The method of claim 48 further comprising contacting an exterior surface of the patient with a cooling blanket.

61. A method of providing hypothermia to a patient comprising:
inserting a fluid delivery member into a peritoneal cavity of the patient;
delivering hypothermia fluid from a fluid source into the peritoneal cavity through the delivery member;
measuring patient temperature in a bladder; and
limiting fluid pressure within the peritoneal cavity without providing feedback control to the fluid source.

62. The method of claim 61 wherein the fluid source comprises a fluid container, the step of limiting fluid pressure further comprising limiting a height of the container over the patient.

63. The method of claim 61 wherein the delivering step comprises commencing delivery of fluid through the delivery member automatically when an outlet port of the delivery member enters the peritoneal cavity.

64. The method of claim 61 further comprising activating a heat exchange element within the peritoneal cavity.

65. The method of claim 61 further comprising cooling the fluid in the cavity using an endothermic reaction.

66. The method of claim 61 further comprising cooling the fluid using a compressed gas.

67. The method of claim 61 further comprising cycling a fixed volume of fluid into and out of the peritoneal cavity.

68. The method of claim 61 wherein the fluid comprises a hypertonic ice slurry and a hypotonic cold fluid.

69. The method of claim 68 wherein the hypertonic ice slurry and a hypotonic cold fluid together are isotonic.

70. The method of claim 61 wherein the inserting step comprises inserting the fluid delivery member transgastrically.

71. The method of claim 61 wherein the inserting step comprises inserting the fluid delivery member transrectally.

72. The method of claim 61 further comprising providing automated circulation to the patient with a CPR machine.

73. The method of claim 61 further comprising contacting an exterior surface of the patient with a cooling blanket.

\* \* \* \* \*